(12) United States Patent
Bricker et al.

(10) Patent No.: US 8,101,807 B2
(45) Date of Patent: Jan. 24, 2012

(54) METHODS FOR CONVERTING GLYCEROL TO PROPANOL

(75) Inventors: Maureen L. Bricker, Buffalo Grove, IL (US); Laura E. Leonard, Oak Park, IL (US); Todd M. Kruse, Oak Park, IL (US); James G. Vassilakis, Naperville, IL (US); Simon R. Bare, Wheaton, IL (US)

(73) Assignee: UOP LLC, Des Plaines, IL (US)

( * ) Notice: Subject to any disclaimer, the term of this patent is extended or adjusted under 35 U.S.C. 154(b) by 454 days.

(21) Appl. No.: 12/342,708

(22) Filed: Dec. 23, 2008

(65) Prior Publication Data

US 2010/0160691 A1    Jun. 24, 2010

(51) Int. Cl.
*C07C 31/20* (2006.01)
(52) U.S. Cl. ........................................ 568/852; 568/868
(58) Field of Classification Search .................. 568/852, 568/868
See application file for complete search history.

(56) References Cited

U.S. PATENT DOCUMENTS

| | | | |
|---|---|---|---|
| 6,291,725 B1 | 9/2001 | Chopade et al. |
| 6,479,713 B1 | 11/2002 | Werpy et al. |
| 6,570,043 B2 | 5/2003 | Elliott et al. |
| 6,677,385 B2 | 1/2004 | Werpy et al. |
| 6,841,085 B2 | 1/2005 | Werpy et al. |
| 6,900,361 B2 | 5/2005 | Elliott |
| 6,982,328 B2 | 1/2006 | Werpy et al. |
| 7,038,094 B2 | 5/2006 | Werpy et al. |
| 2008/0228014 A1 | 9/2008 | Bloom |
| 2008/0274019 A1 | 11/2008 | Beggin et al. |
| 2009/0264686 A1 | 10/2009 | Holladay et al. |

OTHER PUBLICATIONS

PCT Search Report dated Jul. 6, 2010, International Appln No. PCT/US2009/064688, International Filing Date Nov. 17, 2009.

*Primary Examiner* — Sikarl Witherspoon
(74) *Attorney, Agent, or Firm* — David J Piasecki

(57) ABSTRACT

A hydrogenolysis method for converting glycerol into propylene glycol by directing a glycerol containing feed having a pH of about 10 or more to a reaction section including at least one glycerol conversion catalyst and operating at glycerol conversions conditions to form a reaction product including propylene glycol.

22 Claims, 12 Drawing Sheets

METHODS FOR CONVERTING GLYCEROL TO PROPANOL

BACKGROUND OF THE INVENTION (1) Field of the Invention

This invention concerns methods for manufacturing propylene glycol through the hydrogenolysis of glycerol.

(2) Description of the Art

The production of biodiesel utilizes vegetable oils, fats and waste restaurant greases while reducing the U.S. dependence on foreign crude oil. Biodiesel is a renewable, alternative fuel that reduces particulate matter and hydrocarbon emissions. However, for every 9 kilograms of biodiesel produced, about 1 kilogram of a crude glycerol by-product is formed.

A problem that results from refining this crude glycerol into refined glycerol is that the glycerol market cannot absorb it. With plentiful glycerol available, its price and U.S. exports have declined. As a result, much of the crude glycerol by-product of biodiesel production is currently disposed of or is sold at a very minimal price.

This problem may continue to worsen because the U.S. production of biodiesel is expected to continue to grow with a target of 400 million gallons of production by the year 2012. At this production capacity, 3.5 million gallons of crude glycerol will be produced every year. This crude glycerol can be purified by several steps including vacuum distillation to produce USP grade glycerol. However, refining the crude glycerol is complex and expensive.

A problem with crude glycerol from a biodiesel plant is that it requires costly upgrading to achieve a technical grade or USP grade glycerol. Typically, biodiesel producers will acidulate the crude glycerol to remove fatty acids in order to facilitate methanol recovery and recycle. Additional steps must be taken to convert the crude glycerol into a high purity glycerol such as USP glycerol. These additional process steps—which increase the cost of producing USP glycerol—may include ion exchange and/or fractionation. There would be significant operating and capital cost incentives if biodiesel derived glycerol could be sold at a profit as a lower grade product or feedstock such as acidulated glycerol rather than requiring purification.

Glycerol can be converted into propylene glycol by well known methods such as hydrogenolysis. Propylene glycol is a major commodity chemical with a growing market and with an annual production of over 1 billion pounds in the U.S. alone. Some typical uses of propylene glycol are in unsaturated polyester resins, functional fluids (antifreeze, de-icing, and heat transfer), pharmaceuticals, foods, cosmetics, liquid detergents, tobacco humectants, flavors and fragrances, personal care, paints and animal feed.

Today, biodiesel production plants are in need of methods to realize increased income from this bio-based crude glycerol byproduct. If bio-based crude glycerol could be efficiently converted to propylene glycol by hydrogenolysis, then the technology could be used in biodiesel production plants to increase profitability. There is a need, therefore, for improvements to existing glycerol to propylene glycol hydrogenolysis processes so that the processes can operate efficiently and economically using glycerol feedstocks and in particular crude glycerol feedstocks that have been minimally acidulated.

SUMMARY OF THE INVENTION

This invention includes hydrogenolysis processes and methods that are capable of processing a variety of glycerol feeds, including acidulated crude glycerol feeds, to form a higher value propylene glycol product efficiently and economically.

One aspect of this invention are methods for converting glycerol into propylene glycol comprising the steps of: directing a glycerol feed to a pretreatment section; combining a base with the glycerol feed in a blending section to form a basic glycerol containing feed stream having a pH of about 10 or greater; directing the basic glycerol containing feed stream and a hydrogen containing gas to a hydrogenolysis reaction section including at least one reactor and into contact with a glycerol conversion catalyst loaded in the at least one reactor wherein the reactor operates at glycerol conversion conditions sufficient to form a reaction section product including propylene glycol; directing the reaction section product including propylene glycol to a separator to form a hydrogen rich separator off gas and a separator liquid product including propylene glycol; and directing the separator liquid product to purification section and processing the separator liquid in the liquid product purification section by the further steps of:

i. directing the neutralized separator liquid product to a unit operation to remove water and $C_1$-$C_3$ alcohols from the neutralized separator liquid; and ii. directing the essentially water free product including propylene glycol and precipitated salts to a solid/liquid separator to form an essentially solids free product stream including propylene glycol.

Another aspect of this invention includes methods for converting glycerol into propylene glycol comprising the steps of: directing a combined feed including hydrogen and a basic glycerol feed that is adjusted to a pH of from about 10 to about 12 with an aqueous base to a hydrogenolysis reactor including at least one catalyst selected from the group consisting of a Ni/Re catalyst and a Co/Pd/Re catalyst, wherein the reactor operates at glycerol conversion conditions sufficient to form a reaction section product including propylene glycol; and directing the reaction section product including propylene glycol to a separator to form a hydrogen rich separator off gas and a separator liquid product including propylene glycol wherein the concentration of the aqueous base is increased to maintain or increase glycol conversion.

Still another aspect of this invention are methods for converting glycerol into propylene glycol comprising the steps of: directing a combined feed including hydrogen and a basic glycerol feed having a pH of from about 10 to about 12 to a hydrogenolysis reactor including at least one catalyst selected from the group consisting of a Ni/Re catalyst and a Co/Pd/Re catalyst, wherein the reactor operates at glycerol conversion conditions sufficient to form a reaction section product including propylene glycol; and directing the reaction section product including propylene glycol to a separator to form a hydrogen rich separator off gas and a separator liquid product including propylene glycol wherein the basic glycerol feed includes at least 50 wt % glycerol and wherein the reactor pressure is controlled at conditions of pressure, temperature and LHSV sufficient to produce a reaction section product having less than about 1.0 butanediol C mole % selectivity.

DETAILED DESCRIPTION OF THE INVENTION

Figure 1:
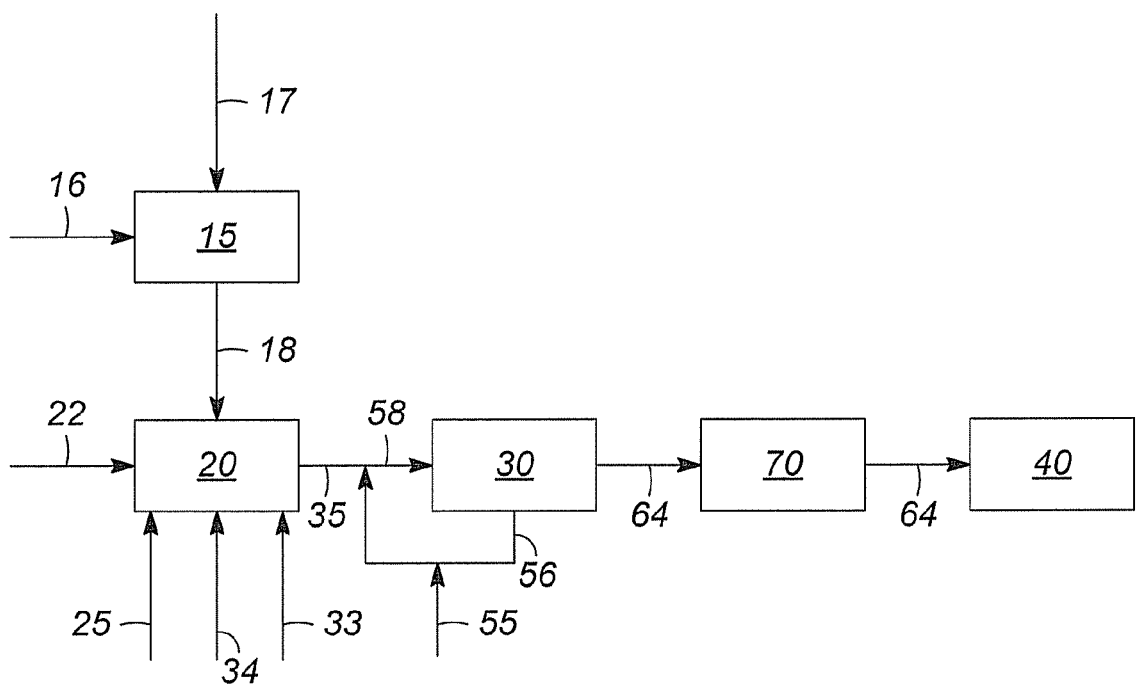
FIG. 1 is a schematic of a process embodiment of this invention for converting glycerol into propylene glycol.
Figure 2:
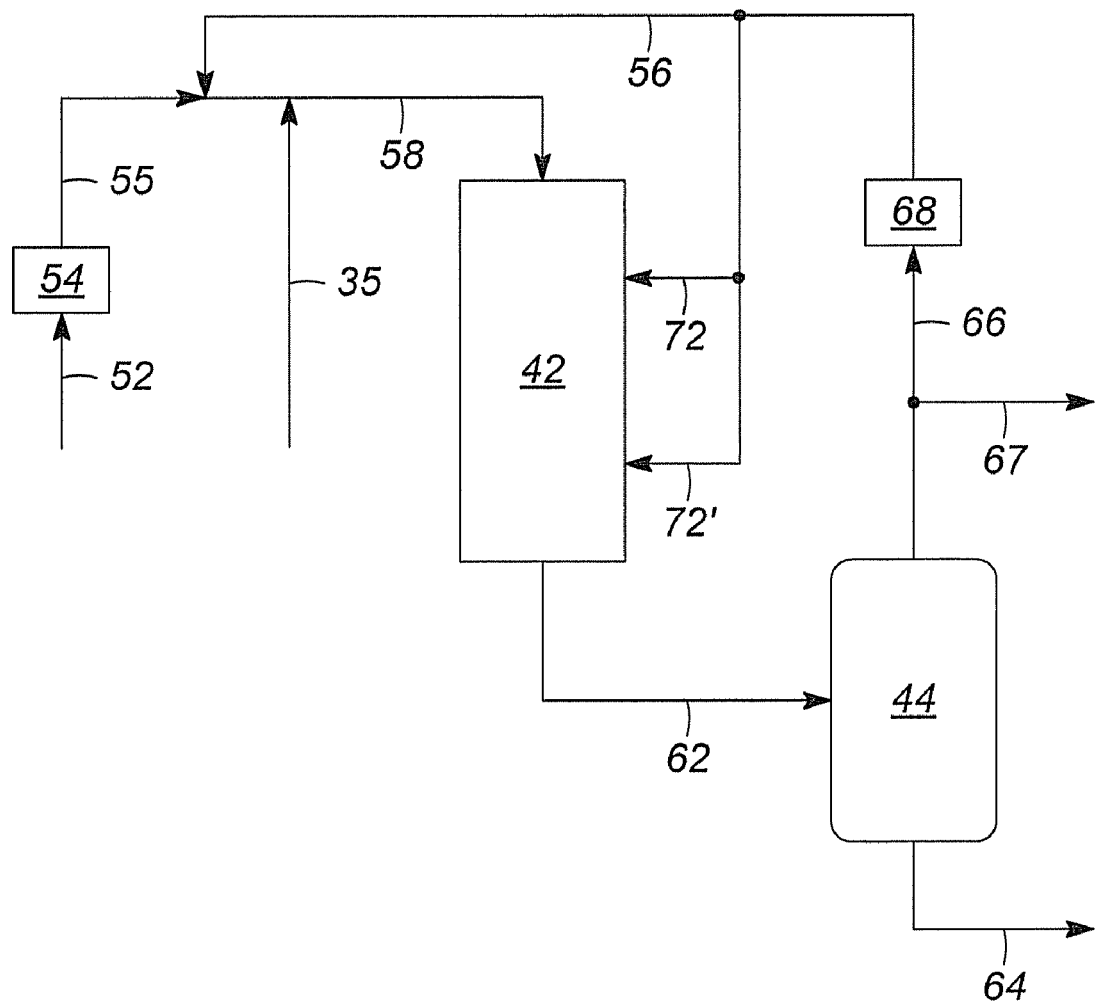
FIG. 2 is a schematic of a reaction section that is useful in the process embodiment of FIG. 1.

The present invention relates to hydrogenolysis processes and apparatuses for converting glycerol into propylene glycol. The processes will be discussed initially with reference to FIGS. 1-3. The glycerol hydrogenolysis process of FIG. 1 includes an optional feedstock pre-treatment section 15, a feed blending section 20, a reaction section 30, and product purification section 40. The process further includes an optional neutralization section 70 for neutralizing the pH of the reaction product before it enters product purification section 40. A purpose of pretreatment section 15 is to pretreat certain crude glycerol feeds before they are directed to feed blending section 20. Glycerol containing feeds that include fatty acids—such as bio-based glycerol feeds—must be pretreated in pretreatment section 15. Pretreatment section 15 includes combining the fatty acid containing glycerol feed 16 with an acid 17, such as sulfuric acid or hydrochloric acid, to form an acidulated glycerol feed 18. The term "acidulated" refers to an acidulated glycerol feed that will contain impurities—other than fatty acids—found in common crude glycerol streams derived from bio-based and other processes. Such impurities can include one or more of methanol, sodium, potassium, tramp impurities, sulfur, iron, nickel, and chloride. Other glycerol feeds such a technical grade glycerol, USP glycerol, technical glycerol and acidulated glycerol can bypass pretreatment section 15 because they do not contain fatty acids.

The purpose of feed blending section 20 is to combine the reaction section feed ingredients including glycerol and to adjust the pH of the glycerol feed to the desired basic pH before the basic glycerol feed is directed to reaction section 30. Several different feeds may be combined in feed blending section 20. A first feed that is directed to pretreatment section 20 is a glycerol feed stream 18 and/or 22.

Glycerol feed stream 22 may be any type of pretreated glycerol feed that has a substantially reduced fatty acid content and, therefore, does not require pretreatment in pretreatment section 15. Fatty acid free glycerol is generally readily available in several grades: pharmaceutical (USP), food additive grade, and technical grade (industrial). Bio-based glycerol that has not been purified is known as crude glycerin. It is common to remove impurities from crude glycerol by vacuum distillation to form a vacuum distilled crude glycerol. However, the processes of this invention do not require vacuum distilled crude glycerol. Instead, splitter's crude glycerol, an 85% glycerin grade recovered and concentrated from the water of hydrolysis; also known as hydrolyzer crude glycerin, or acidulated glycerol are useful feeds. Soap lye crude could also be used as long as the fatty acids are removed; and an ester crude could be used which is produced from the transesterification of vegetable oils.

Glycerol feed streams 18 and 22 may also include methanol as a byproduct of bio-based processes. Methanol may be present in glycerol feed streams 18 and 22 in any amount that does not interfere with the hydrogenolysis reaction. Typically glycerol feed streams 18 and 22 may include up to about 10 wt % methanol and more typically no more than about 1.5 wt % methanol.

Another feed that will be directed to feed blending section 20 is an aqueous base feed 33. Any base that would be understood by one skilled in the art to be useful for adjusting the pH of the chosen glycerol feed to the desired basic pH may be used. The aqueous bases will typically be selected from those that meet one or more criteria of ready availability; little detrimental impact on catalyst activity; inexpensive; and that avoid corrosion issues. Examples of some useful bases are aqueous solutions of NaOH, KOH, ammonium hydroxide, other alkali metal hydroxides, alkoxides and so forth with NaOH and KOH being preferred. The amount of base in the base feed will typically range from about 0.5 to about 5.0 wt % depending upon the base chosen. If the pH is adjusted with NaOH, the concentration of NaOH in the aqueous solution will be from about 0.1 to about 5.0 wt %, and preferably from about 0.5 to about 1.5 wt %. If KOH is the chosen aqueous base, then the concentration of a preferred aqueous solution of KOH will be from about 0.5 to about 2.0 wt %

A glycerol recycle stream 25 from product purification section 40 may also be directed to feed blending section 20. Other ingredients—both solid and liquid—that may be added to the reactor feed in feed blending section 20 include, but are not limited to, water, $C_1$-$C_3$ alcohols, salts, polyols and any other feed ingredients know to one skilled in the art.

Feed blending section 20 includes at least a pH adjustment step where the base feed 33 is combined with glycerol feed stream 18 and/or 22 to form a basic glycerol feed stream 35 having the target pH. The basic glycerol feed 35 will include from about 20 to about 80 wt % glycerol and preferably from about 40 to about 60 wt % glycerol with the remainder being mainly water. A recycle water stream 34 from purification section 40 may also be combined with the glycerol and base in feed blending section 20. Water is produced in the hydrogenolysis reaction and is also part of the basic glycerol reactor feed streams 18 and 22. Water is blended into the feed in feed blending section 20 to adjust the glycerol content of the basic glycerol feed to the desired level. By using recycled process water stream 34 for any water adjustment needs, the only water that is added to the reactor is the initial water and the overall process water use is neutral.

Feed blending section 20 can optionally include a solid liquid separation step. In this embodiment the acidulated glycerol is mixed with base and any salts that precipitate are removed in a solid/liquid separation step. Thereafter the essentially solid free basic glycerol is diluted with water (or alternate solvent) to the desired glycerol concentration.

Feed blending section 20 may be any type of unit operation that effectively admixes two or more miscible liquids. One example of a feed blending section 20 is an inline mixing apparatus in which the liquid feed ingredients are directed and admixed with one another to form the basic glycerol feed 35. Alternatively, feed blending section 20 may be a surge tank in which the feed ingredients are combined in a controlled manner in order to carefully control the pH of basic glycerol feed 35. The basic glycerol feed 35 exiting feed blending section 20 will have a basic pH. More preferably the basic glycerol feed will have a pH of from about 10 to 12 and most preferably a pH of about 12. High feed pH is one important variable that helps maximize propylene glycol selectivity.

Next the basic glycerol feed 35 is directed to reaction section 30. Reaction section 30, shown in FIG. 2, includes a fixed bed catalyst reactor 42, high pressure separator 44, and hydrogen recycle loop. Reactor 42 is maintained at the desired reaction pressure with hydrogen. A makeup hydrogen containing gas stream 52 is compressed with makeup hydrogen compressor 54 to form a compressed make up gas stream 55 which in turn is combined with recycle hydrogen stream 56 and then with basic glycerol feed 35 to form combined feed stream 58. Combined feed stream 58 is then heated to the desired reaction temperature and then directed into reactor 42.

The make-up hydrogen containing gas stream 55 may be any hydrogen rich gas stream that is available at the process site. The make-up hydrogen containing gas should include at least about 70 wt % hydrogen and preferably at least about 85 wt % hydrogen and most preferably more than 95 wt % hydrogen. Moreover, the make-up hydrogen containing gas stream 55 can be pure hydrogen. Finally, the make up hydrogen containing gas should be essentially free of compounds and impurities that could have a detrimental impact on catalyst activity and/or reaction selectivity.

Heated combined feed stream 58 contacts at least one catalyst in reactor 42 which operates at glycerol conversion conditions of pressure, temperature and space velocity to form a hydrogenolysis reaction product stream 62 that includes propylene glycol. Reactor product stream 62 is directed to gas/liquid separator 44 to form a high pressure separator liquid product 64 which is directed to purification section 40. A high pressure separator gas product stream 66 is also formed in high pressure separator 44. The high pressure separator gas product stream 66 is directed at least in part to recycle compressor 68 where it is compressed to form recycle gas stream 56 which is then admixed with make-up hydrogen stream 55. The make-up hydrogen can be combined with the recycle hydrogen stream either before or after recycle compressor 68. Moreover, a portion of the high pressure separator gas product stream may be removed from the process as slip stream 67, for example to control the accumulation of undesirable gaseous by-products.

In a preferred embodiment, reactor 42 includes one or more quench streams 72 and 72' for quenching the exothermal hydrogenolysis reaction. Quench streams 72 and 72' are shown as being hydrogen but they may be any liquid or gas that is available within the process. The quench stream 72 will be provided in a sufficient number and will include one or more quench streams operating at rates sufficient to prevent the temperature across the reactor catalyst beds from rising more than from about 10° F. to 80° F. and more preferably from rising more than about 10 to 40° F. Where multiple catalyst beds are used, the average temperature of each catalyst bed will fall within the range of average catalyst bed temperatures recited above.

Reaction section 30 may include one or more reactors loaded with a solid hydrogenolysis catalyst. A preferred reaction section 30 will include a single reactor 42 with a fixed bed of solid catalyst with optional quench zones. Under hydrogenolysis reaction conditions, reactor 42 will operate as a trickle bed reactor.

Any catalyst that is known to be useful in converting glycerol to propylene glycol in the presence of hydrogen may be used in reaction section 30 of this invention. Examples of useful catalysts include copper/chromite; copper zinc and copper oxide with BaO, MgO, CaO, and Mo as additives for activity or stability; mixtures of cobalt, copper, manganese and molybdenum. More preferred catalysts are heterogeneous catalysts such as CoPdRe or NiRe on a solid support such as carbon wherein the metals are reduced. Examples of some useful catalysts are disclosed in U.S. Pat. Nos. 6,479,713, 7,038,094; 6,982,328; 6,900,361; 6,841,085; 6,677,385, 6,570,043; the specifications of each of which are incorporated herein by reference. Particularly preferred catalysts are those disclosed in U.S. patent application Ser. No. 12/082,997, the specification of which is also incorporated herein by reference.

Reactor 42 is operated at reaction conditions that promote the conversion of glycerol to propylene glycol. The reaction conditions include catalyst bed temperatures of between 300° F. and 500° F., and preferably between 325° F. and 400° F. In some instances the catalyst bed temperatures—including the ranges recited above—will be identified as average catalyst bed temperatures. Otherwise the temperatures refer to temperatures measured at any point in a single catalyst bed. The reactor catalyst volume will be sufficient to achieve a liquid hourly space velocity (LHSV) of glycerol of $0.1$-$5.0$ $hr^{-1}$ based upon the selected glycerol feed rate. The reaction conditions further include a reactor pressure of from about 400 to about 2400 psig. The hydrogen rate to the reactor is typically from about 2-20 mole hydrogen per mole glycerol feed into reactor 42.

The high pressure separator liquid product stream 64 is directed to purification section 40. In most instances, the separator liquid product stream 64 will be neutralized in neutralization section 70 before being subjected to subsequent unit operations. However, it may be desirable in some instances to neutralize the propylene glycol containing product stream as it is being processed in purification section 40. The design of purification section 40 is dependent on the purity of the propylene glycol product produced in the reactor section. The first step of product purification is to remove the water and the $C_1$-$C_3$ alcohols. The alcohols are recovered from the water in a fractionation column. The mixed alcohol stream is recovered and contains less than about 10% water and preferably less than about 3% water. The essentially water free product stream is directed to a second column. If the butane diol by-product concentration in the liquid product is sufficiently low, the propylene glycol product can be recovered directly as the overhead product from the second column. In this embodiment the second column bottom product contains ethylene glycol, unconverted glycerol, sodium salts and other heavy products such as dipropylene glycol and is directed to a solid/liquid separator to remove solids.

Figure 3:
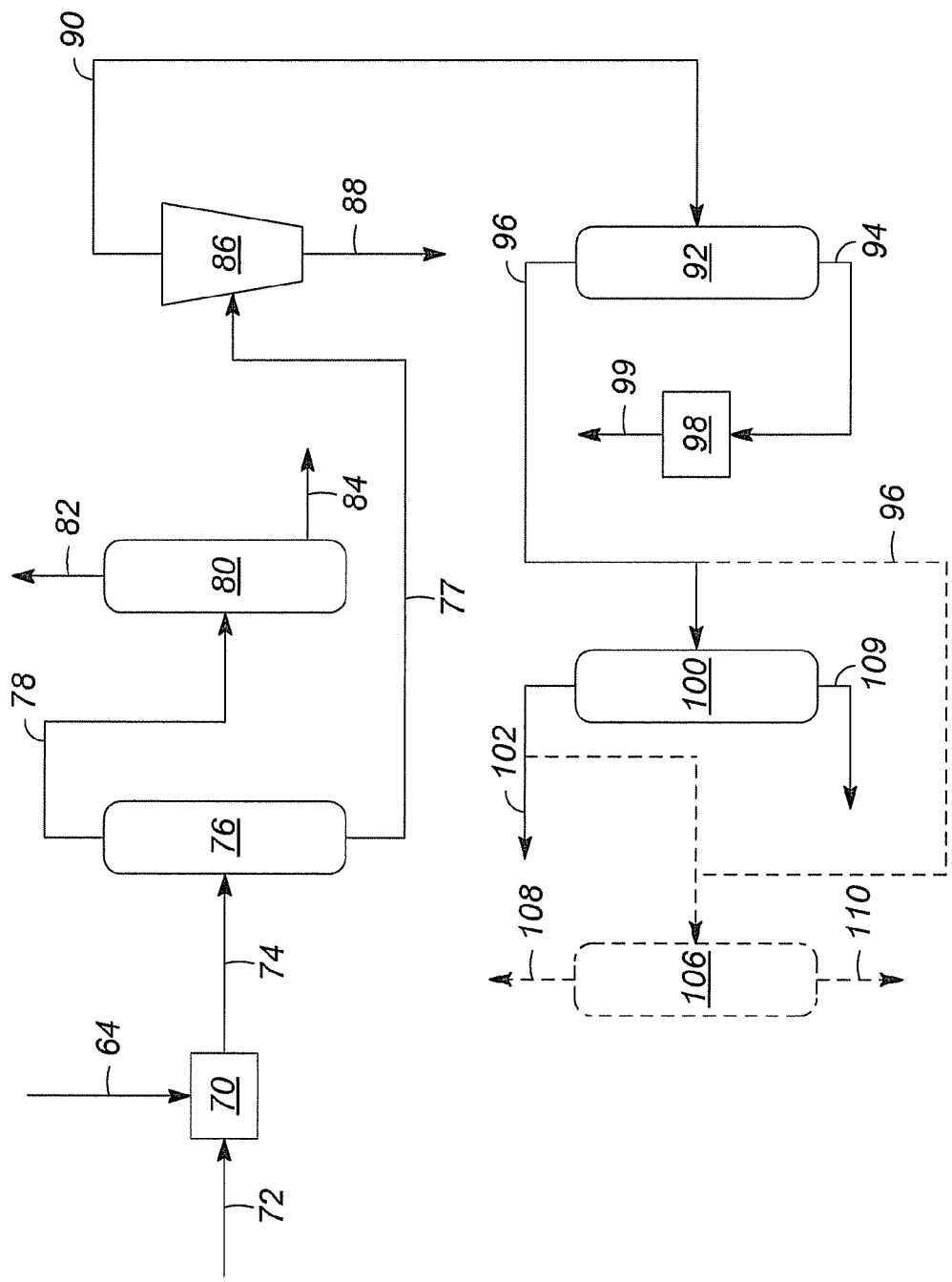
FIG. 3 is a schematic of a purification section that is useful in the process embodiment of FIG. 1.

A detailed purification section embodiment is shown in FIG. 3 which includes an acidification section 70 where an acid stream 72 such as sulfuric acid or hydrochloric acid is combined with liquid product stream 64 to form a pH adjust liquid product stream 74 having a pH of about 7 to about 7.5. The pH adjusted liquid product stream 74 is then directed to stripper 76 operating at conditions sufficient to form a stripper overhead stream 78 including water and light ($C_1$-$C_3$) alcohols. The stripper overhead stream is then directed to fractionation column 80 that operates at conditions sufficient to form an overhead product stream 82 consisting essentially of light alcohols and a bottoms stream 84 consisting of essentially water that may be recycled back to feed blending section 20, sent to disposal, or both.

Stripper 76 also has a stripper bottoms stream 77 that includes, propylene glycol, unreacted glycerol, hydrogenolysis byproducts such as ethylene glycol, and butanediols as well as solids such as salts that precipitate as water is removed from pH adjusted liquid product stream 74 in stripper 76. The stripper bottoms stream 77 is directed to a solid/liquid separator 86 to separate the solids in the stripper bottoms stream 77 from the liquids. Any device that is able to separate solids from liquids many be used. Non-limiting examples of useful solid/liquid separators are drum filters and hydroclones. The solids 88, removed from solid/liquid separator 86 are recovered or disposed of. The liquid product 90 from solid/liquid separator 86 is next directed to fractionation column 92. One purpose of fractionation column 92 is to separate heavy materials such as unreacted glycerol and heavy polyols as the fractionation column 92 bottom stream 94 from the propylene glycol product as the fractionation column 92 overhead stream 96. It is also possible to operate fractionation column 92 to recover ethylene glycol in column bottoms stream 94 as well in order to produce a column overhead stream 96 that is a salable propylene glycol.

If the glycerol in bottoms stream 94 is to be recycled back to feed blending zone 20, then bottoms stream 94 is directed to wiped film evaporator 98 or to a similar solid/liquid separator to remove any final unwanted salts from bottoms stream 94 before it is returned to the feed blending section as recycle glycerol stream 99.

If overhead stream 96 includes unacceptable levels of ethylene glycol, then a propylene glycol/ethylene glycol splitter column 100 will be used to form an essentially ethylene glycol free salable propylene glycol product stream. Otherwise, overhead stream 96 can be directed to optional polishing column 106 or sold as salable propylene glycol product. Whether or not propylene glycol/ethylene glycol splitting is necessary will depend on the application since in some applications the ethylene glycol specification in the final purified propylene glycol product could be 100-1000 wppm and possibly lower due to its toxicity. Since ethylene glycol is boiling point is greater than the boiling point of propylene glycol, the overhead stream 102 of splitter column 100 will include essentially ethylene glycol free propylene glycol while the bottoms product stream 104 will include ethylene glycol.

The column 92 overhead stream 96 may be sold as a commercial product if the polypropylene glycol purity is high enough and if the ethylene glycol content of the stream is at acceptable levels. It is preferred that the final propylene glycol product is essentially ethylene glycol free and has a purity greater than 99%, and more preferably greater than about 99.5% purity. In addition, streams 96 or 102, if sold as salable propylene glycol must be low in certain hydrogenolysis byproducts. The hydrogenolysis process produces several byproducts in detectable amounts. Most troublesome are byproducts with boiling points similar to the boiling point of propylene glycol (188° C.). Such similar boiling byproducts include 2,3-butanediol (184° C.), ethylene glycol (196-198° C.), and 1,2-butanediol (192° C.).

In most instances, streams 96 and/or 102 will include an unacceptably high amount of these byproducts. If streams 96 and/or 102 include more that about 1.0 wt %, more preferably 0.5 wt % and most preferably 0.2 wt % of these products then the propylene glycol product streams may require further processing in polishing column 106. If polishing is required, then polypropylene product stream 96 or 102 is directed to polishing column 106 to remove the unwanted byproducts in overhead stream 108 and to form a final propylene glycol product stream 110.

EXAMPLES

Example 1

A. Catalyst Preparation

A Co/Pd/Re catalyst including 2.5 wt % Co, 0.4 wt % Pd, and 2.4 wt % Re on Norit ROX 0.8—an acid washed extruded steam activated carbon—was prepared using the catalyst preparation examples from U.S. patent application Ser. No. 12/082,997, the specification of which is incorporated herein by reference. The catalyst was reduced at 320° C. under H2 prior to use.

B. Pilot Plant Operation

Glycerol hydrogenolysis tests were performed using the catalysts prepared above in a pilot plant. The pilot plant included a single reactor. The catalyst (150 cc) was loaded into the reactor with an inert solid diluent material (95 cc) to dilute the bed. The purpose of the diluent is to lengthen the catalyst bed to improve the flow characteristics through the bed and to spread the heat of reaction allowing the reactor to operate essentially isothermally. The catalyst bed was topped with 40 cc of inert material to act as a preheat section.

The reactor was operated in a once through feed mode—the glycerol feed was combined with pure header hydrogen and sent to the reactor. The glycerol feeds used in the various examples are set forth in Table 1 below:

TABLE 1

| Feedstock Composition | | 1 USP Glycerol | 2 Commercial Acidualated Glycerin | 3 Commercial Acidualated Glycerin | 4 USP Glycerol |
|---|---|---|---|---|---|
| Sodium Sulfate | wt % | 0.00 | 3.35 | 3.35 | 0.00 |
| Water by KF | wt % | 58.89 | 54.53 | 52.80 | 40.26 |
| NaOH | wt % | 1.04 | 0.77 | 1.14 | 0.97 |
| Glycerol | wt % | 40.07 | 37.67 | 38.92 | 58.26 |
| Ethylene Glycol | wt % | 0.00 | 0.00 | 0.00 | 0.11 |
| Propylene Glycol | wt % | 0.00 | 0.00 | 0.00 | 0.00 |
| Methanol | wt % | 0.00 | 3.63 | 3.79 | 0.37 |
| Acetic Acid | wt % | 0.00 | 0.05 | 0.00 | 0.04 |
| Total | wt % | 100.00 | 100.00 | 100.00 | 100.00 |

All feeds were adjusted to a pH of about 12 using NaOH prior to use.

The pilot plant reactor temperature was controlled by submerging the reactor in a continuously stirred bath. The reactor effluent was directed to a high pressure separator operating at the reactor pressure which separated the un-dissolved gas from the liquid phase. The rate of the gas stream exiting the high pressure separator was measured with a wet test meter. The liquid leaving the HPS was collected as the liquid product for analysis.

In a first pilot plat run, the stability of the catalyst performance was evaluated using feedstocks prepared from USP glycerol and a glycerol feed from biodiesel conversion that included methanol. The pilot plant process conditions were:

| Glycerol Feed | 1, 2 & 3 |
|---|---|
| H2/Glycerol m:m | 5.0 |
| Pressure | 1200 psi |
| Temperature | 374° F. |
| Glycol LHSV | 1.17 hr$^{-1}$ |
| Feed pH | ~12 |
| Glycol Feed Wt % | 39-40 |

Figure 4A:
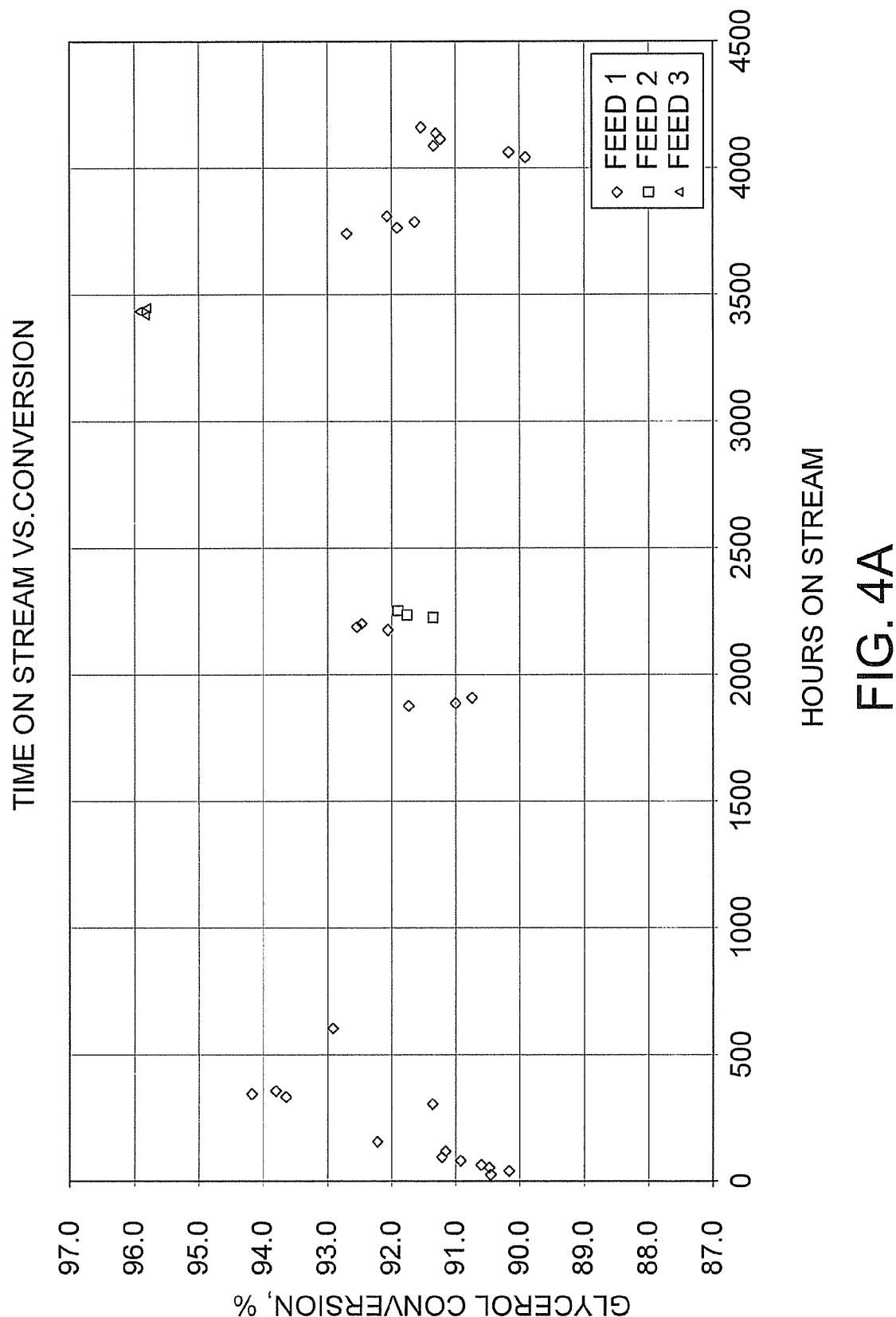
FIGS. 4A and 4B are plots demonstrating process stability (selectivity and conversion) over time.
Figure 4B:
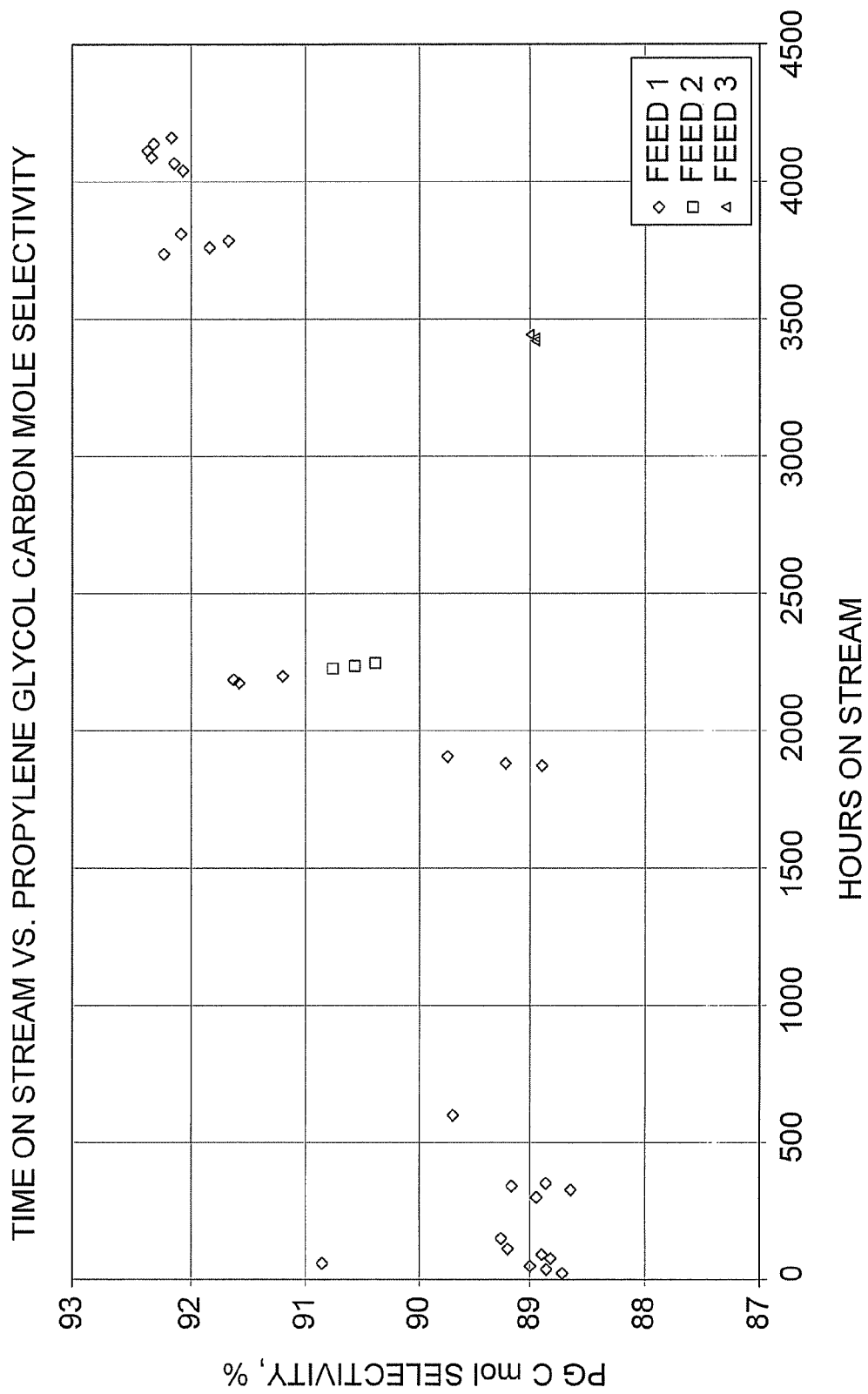
Figure 5:
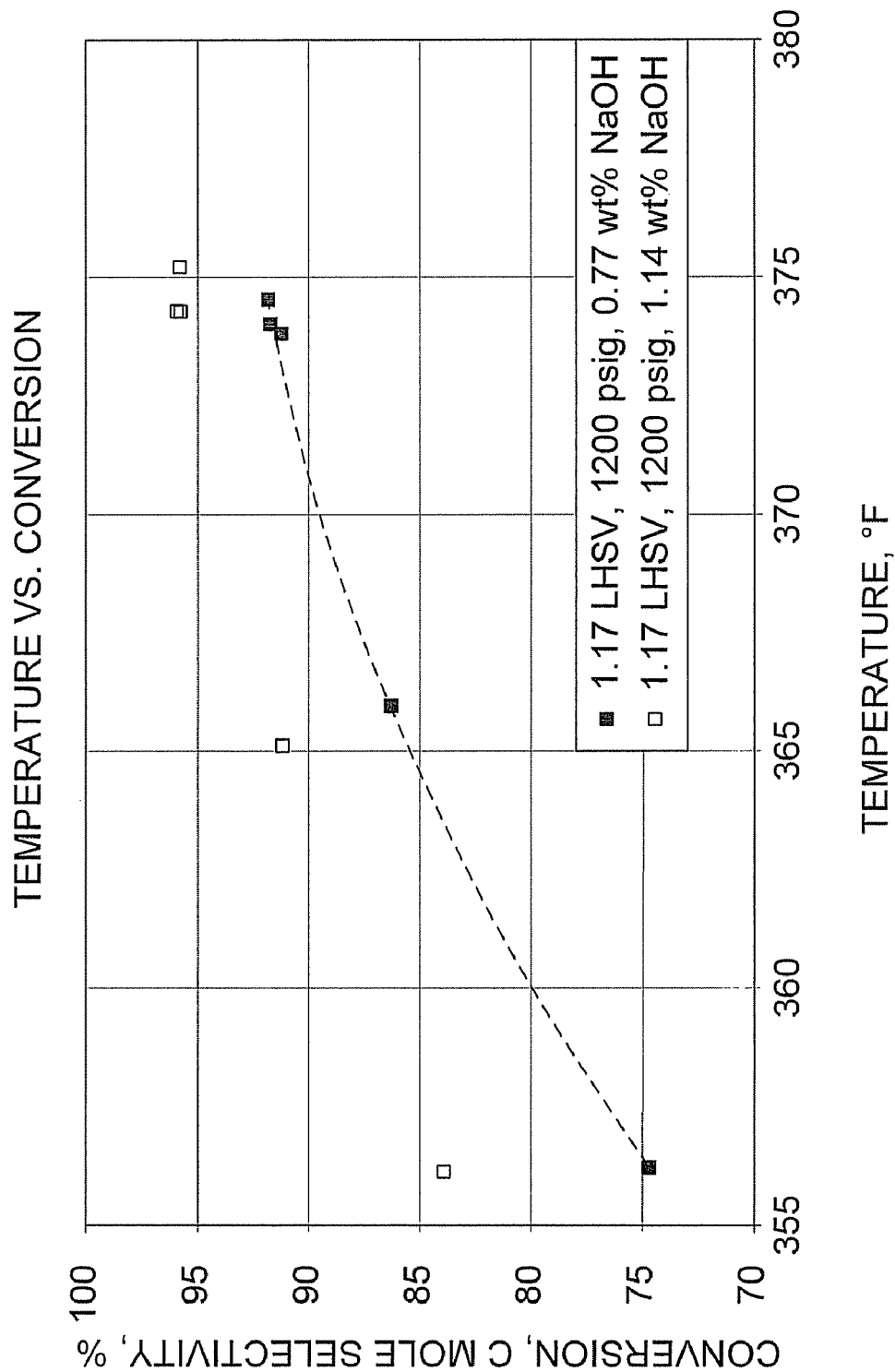
FIGS. 5-8 are plots of the impact over a range of temperatures of increasing the feed base concentration on glycerol conversion and selectivity.
Figure 6:
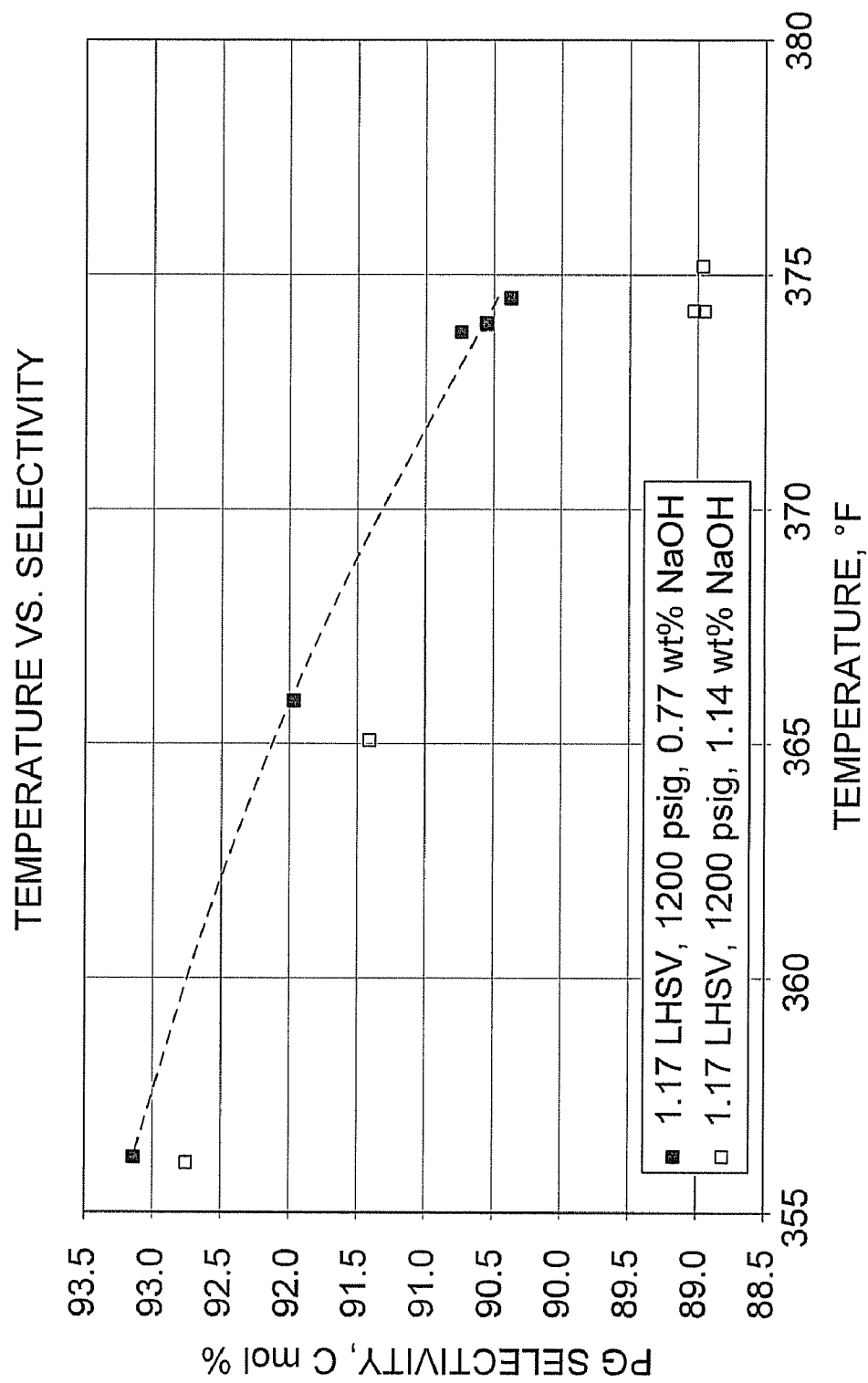
Figure 7:
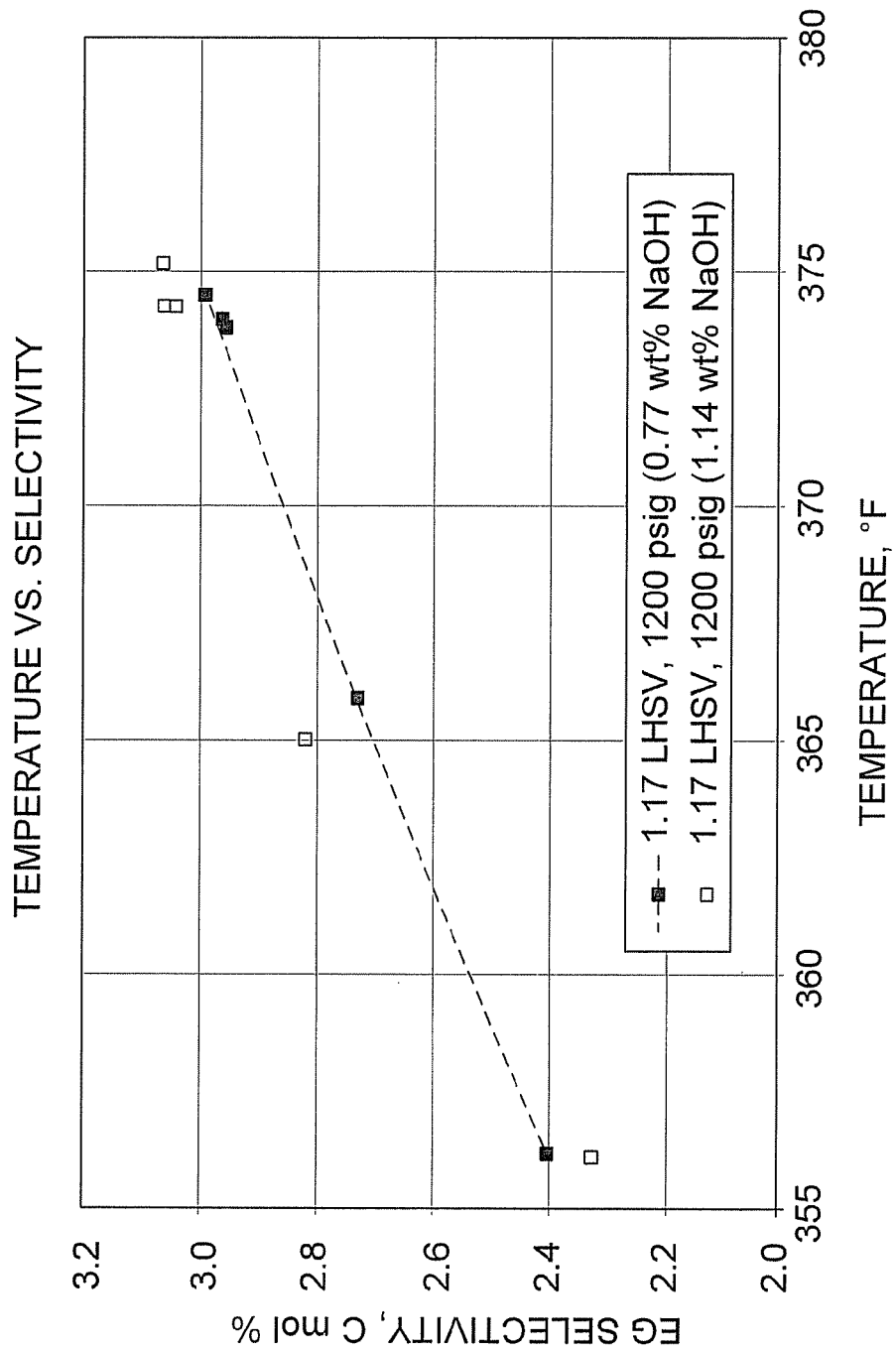
Figure 8:
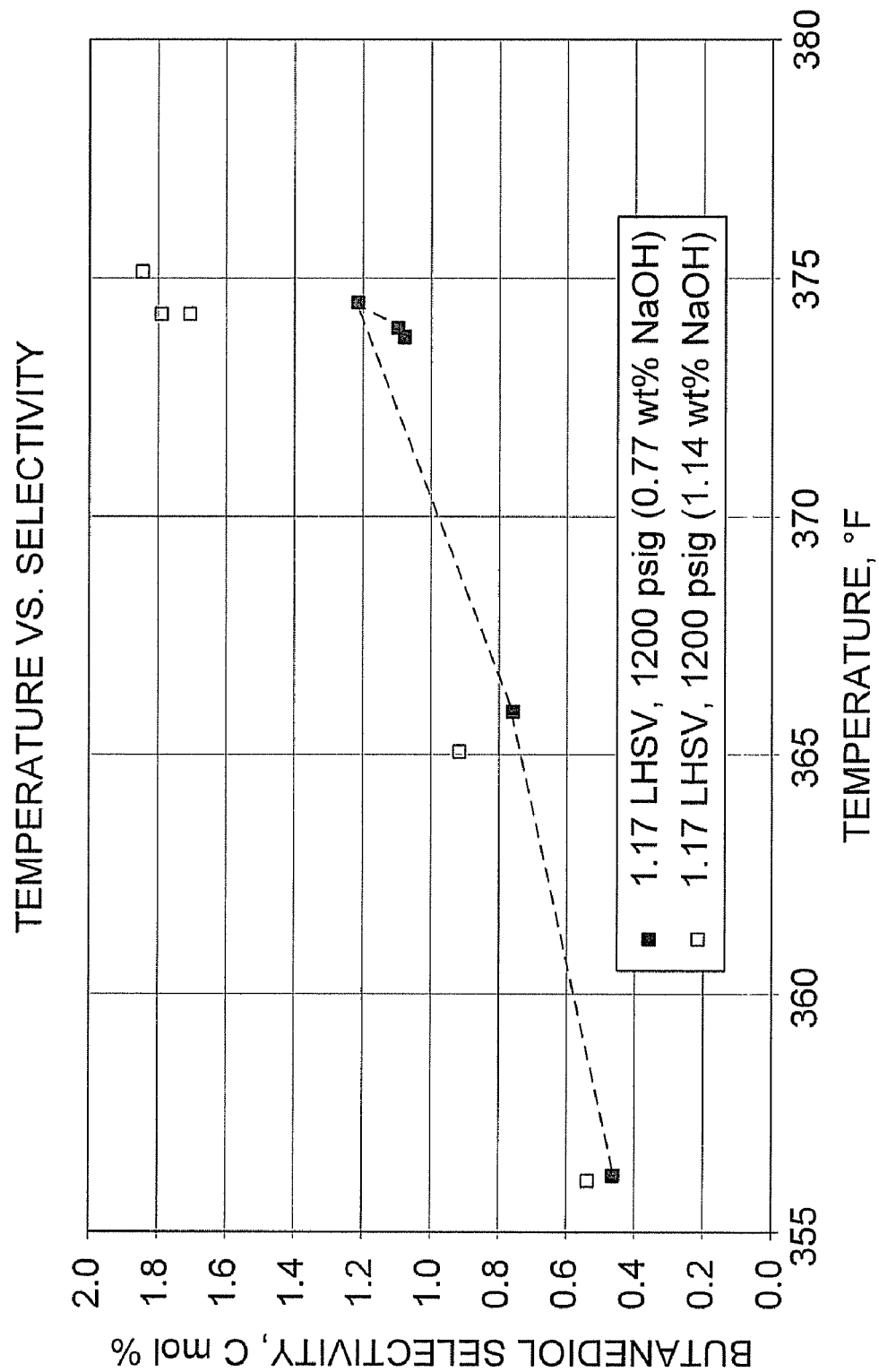

The stability results over time are shown in FIGS. 4A and B. The catalyst demonstrated stable performance for >4000 hours while processing both USP glycerol feedstock and commercially acidulated feedstock high salt content (>3 wt % sodium sulfate) and containing >3% methanol. Stable performance has also been demonstrated with HCl acidulated feedstock. However, sulfuric acid acidulated feedstock is preferable due to metallurgy issues related to high concentrations of chloride in aqueous systems.

Example 2

It is routine in fixed bed processes to raise the reactor temperature as the catalyst ages with time on stream and becomes less effective in order to maintain catalyst conversion and/or product yields. In the case of converting glycerol to propylene glycol, increasing the reactor temperature to compensate for catalyst deactivation does maintain glycerol conversion. However, the increased reaction temperature has a detrimental effect upon glycerol selectivity. Most importantly, the amount of ethylene glycol and butane diol—reaction byproducts—increases at higher reactor temperature while the reactor propylene glycol selectivity decreases with increasing reactor temperature. This is problematic not only from a propylene glycol yield perspective, but it also impacts product purification. The purification section must separate ethylene glycol, propylene glycol and 2,3-butanediol from one another to achieve a high purity propylene glycol product. This separation is very challenging due to the relatively small differences in the boiling points (<10° C.) of the three compounds. As a result, changes in the reaction product yield ratios of the three products over the cycle length will have a significant impact on the design of the product purification section and the operation of the fractionation steps to separate the close boiling glycols.

In this example, we surprisingly found that we could maintain glycerol conversion while at the same time minimizing the increase in the reactor temperature required to compensate for catalyst deactivation resulting in little product yield deviation. More particularly we have surprisingly discovered that small changes in the base concentration have a significant impact on the catalyst performance.

We loaded the catalyst of Example 1A into the pilot plant of Example 1B and we operated the reactor at 356° F. to 375° F., 1.17 LHSV, 1200 psig, and 5:1 hydrogen to glycerol molar ratio using feed number 2 and 3 from Table 1 above. At these conditions, we evaluated the process conversion and selectivities at base concentrations used to adjust the glycerol feed pH to about 12 from 0.77 wt % NaOH to 1.14 wt %. The pilot plant results are plotted in FIGS. 5-8 and are summarized in Table 2 below.

TABLE 2

| | Feed # | | |
|---|---|---|---|
| | 2 | 2 | 3 |
| NaOH Concentration, wt % | 0.77 | 0.77 | 1.14 |
| Temperature, ° F. | 356 | 366 | 356 |
| Glycerol Conversion, % | 74.8 | 86.4 | 84.0 |
| Propylene Glycol Selectivity, C mol % | 93.1 | 92.0 | 92.8 |
| Ethylene Glycol Selectivity, C mol % | 2.4 | 2.7 | 2.3 |
| Butanediol Selectivity, C mol % | 0.5 | 0.8 | 0.5 |

Increasing the NaOH concentration resulted in the glycerol conversion increasing more than 9% from 74.8% to 84.0%. The changes in the product selectivity due to the change in the base concentration were small. With 1.14 wt % base the propylene glycol selectivity was 92.8 C mol % compared to 93.1 C mol % at 0.77 wt % NaOH. If the temperature was increased (to about 365° F.—See FIG. 5) to achieve similar glycerol conversion with 0.77 wt % NaOH the propylene glycol selectivity would be lower, at 365° F. with 0.77 wt % base as NaOH the glycerol conversion was 86.4% and the propylene glycol selectivity was 92.0 C mol %.

The ethylene glycol selectivity at 356° F. was 2.4 and 2.3 C mol % at 0.77 wt % NaOH and 1.14 wt % NaOH respectively, operating at 365° F. to achieve 86.4% glycerol conversion resulted in the ethylene glycol selectivity increasing to 2.7 C mol %. Adjusting the base concentration rather than the reactor temperature to achieve the desired conversion has a pronounced impact on ethylene glycol and butanediol selectivity.

The ethylene glycol and butane diol selectivities are more sensitive to changes in reaction temperature than to changes in base concentration. We have, therefore, discovered that increasing the base concentration in the feedstock to compensate for catalyst deactivation with age is preferable to raising temperature to compensate for catalyst aging and deactivation. As a result, maintaining a lower end of run reactor temperature by increasing the base concentration to compensate for the catalyst deactivation results in a lower cost product purification section and/or a higher purity product due to the lower concentrations of ethylene glycol and butanediols in the reaction product.

The increased base level will result in additional sodium salts. However, these byproducts are easily separated from the propylene glycol product in comparison to the difficulties involved in separating ethylene glycol and butane diol byproducts which have boiling points close to the boiling point of the propylene glycol product.

Example 3

Figure 9:
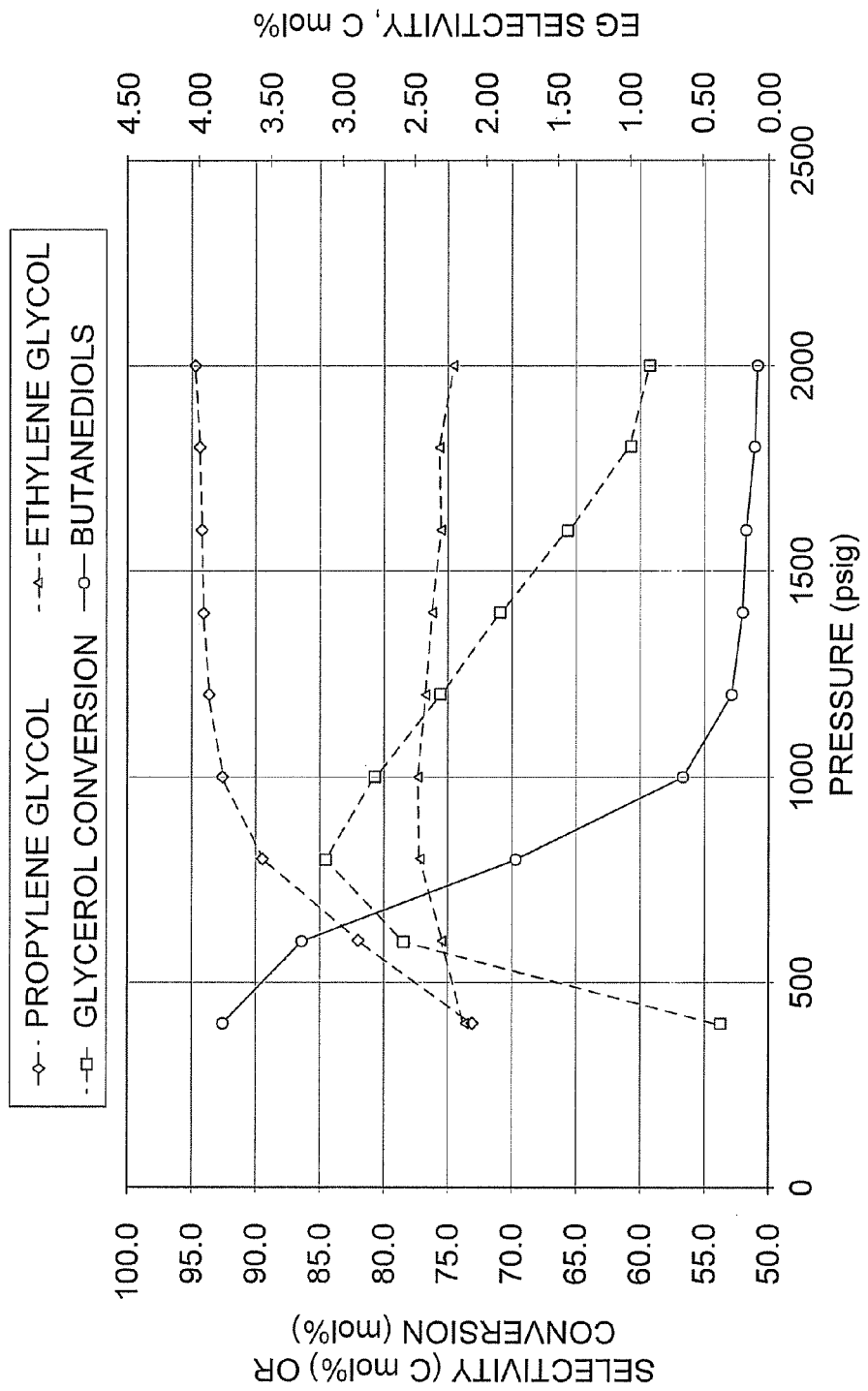
FIG. 9 is a plot of the impact reactor pressure on glycerol hydrogenolysis conversion and product selectivities using a low wt % glycerol feed.

This example investigates methods for achieving high glycerol conversions and high propylene glycol selectivity's for reactor feeds containing concentrations of glycerol >50 wt %. As the hydrogen pressure in the reactor is increased, the selectivity to propylene glycol increases while the glycerol conversion passes through a maximum. For a feed containing a low concentration of glycerol, such as 40 wt %, this maximum glycerol conversion point is around 1000-1200 psig. (See FIG. 9, Feed 1) However, for a 60 wt % glycerol feed (Feed 4), the glycerol conversion and propylene glycol selectivity both increase when pressure is increased up to 1800 psig.

Catalyst from Example 1A was loaded into the reactor of the pilot plant described in Example 1B. The reactor was operated at temperatures of 356° F. and 374° F. and at pressures of 1200 psig and 1800 psig. The reactor conditions and results are reported in Tables 3 and 4 below.

TABLE 3

| LHSV hr$^{-1}$ | 0.50 | 0.50 |
|---|---|---|
| Temperature, ° F. | 356 | 356 |
| Pressure, psig | 1200 | 1800 |
| Glycerol Conversion, % | 98.0 | 95.5 |
| Propylene Glycol Selectivity, C mol % | 89.6 | 94.0 |
| Ethylene Glycol Selectivity, C mol % | 2.7 | 2.6 |
| Butanediol Selectivity, C mol % | 1.6 | 0.3 |

TABLE 4

| LHSV hr$^{-1}$ | 0.50 | 0.50 |
|---|---|---|
| Temperature, ° F. | 374 | 374 |
| Pressure, psig | 1200 | 1800 |
| Glycerol Conversion, % | 98.0 | 99.7 |
| Propylene Glycol Selectivity, C mol % | 84.7 | 91.2 |

TABLE 4-continued

| | | |
|---|---|---|
| Ethylene Glycol Selectivity, C mol % | 3.2 | 3.3 |
| Butanediol Selectivity, C mol % | 2.5 | 0.8 |

The results reported in Tables 3 and 4 demonstrate that operating the reactor at a temperature of 374° F. and 1800 psig, will achieve a glycerol conversion of >99.7% glycerol while maintaining a propylene glycol selectivity of >91%. In addition, at this pressure the reactor temperature can be lowered to 356° F. to achieve a glycerol conversion of about 95.5% and propylene glycol selectivity of about 94.0%.

Both of these conditions are independently advantageous. First, the condition at 356° F. and 1800 psig leads to a very low selectivity to byproducts such as butanediols which can greatly lower the costs of the product purification scheme. These conversions and selectivities are very similar to those that can be achieved with lower glycerol feed concentrations at the same LHSV and same temperature. Next, the condition at 374° F. and 1800 psig leads to near 100% conversion of glycerol. At such a high conversion of glycerol, a glycerol recycle may no longer be required which eliminates the need for a costly glycerol purification section needed for a glycerol recycle stream.

To make use of this surprising finding, the reactor must be designed to withstand reactor pressures up to and exceeding 1800 psig at elevated temperatures. By designing for this pressure, the process will have tremendous flexibility in being able to handle higher glycerol feed concentrations up to 60 wt % by operating at 1800 psig. By operating at 374° F., 1800 psig, and 0.5 LHSV with a 60 wt % glycerol feed, a glycerol recycle may no longer be needed and any glycerol recycle built into the process could be taken offline to save operating expenses.

Example 4

In this example we investigated whether or not glycerol conversion could be improved while operating the reactor at a low temperature by increasing the catalyst volume. The catalyst and pilot plant of Example 1 was used in this example. The reactor was operated at an $H_2$/glycerol molar feed ratio of 5.0, a pressure of 1200 psig, a temperature of 356° F. and with glycerol feedstock 1 from Table 1. The LHSV was varied in this run from 0.5 to 3 $hr^{-1}$.

Figure 10:
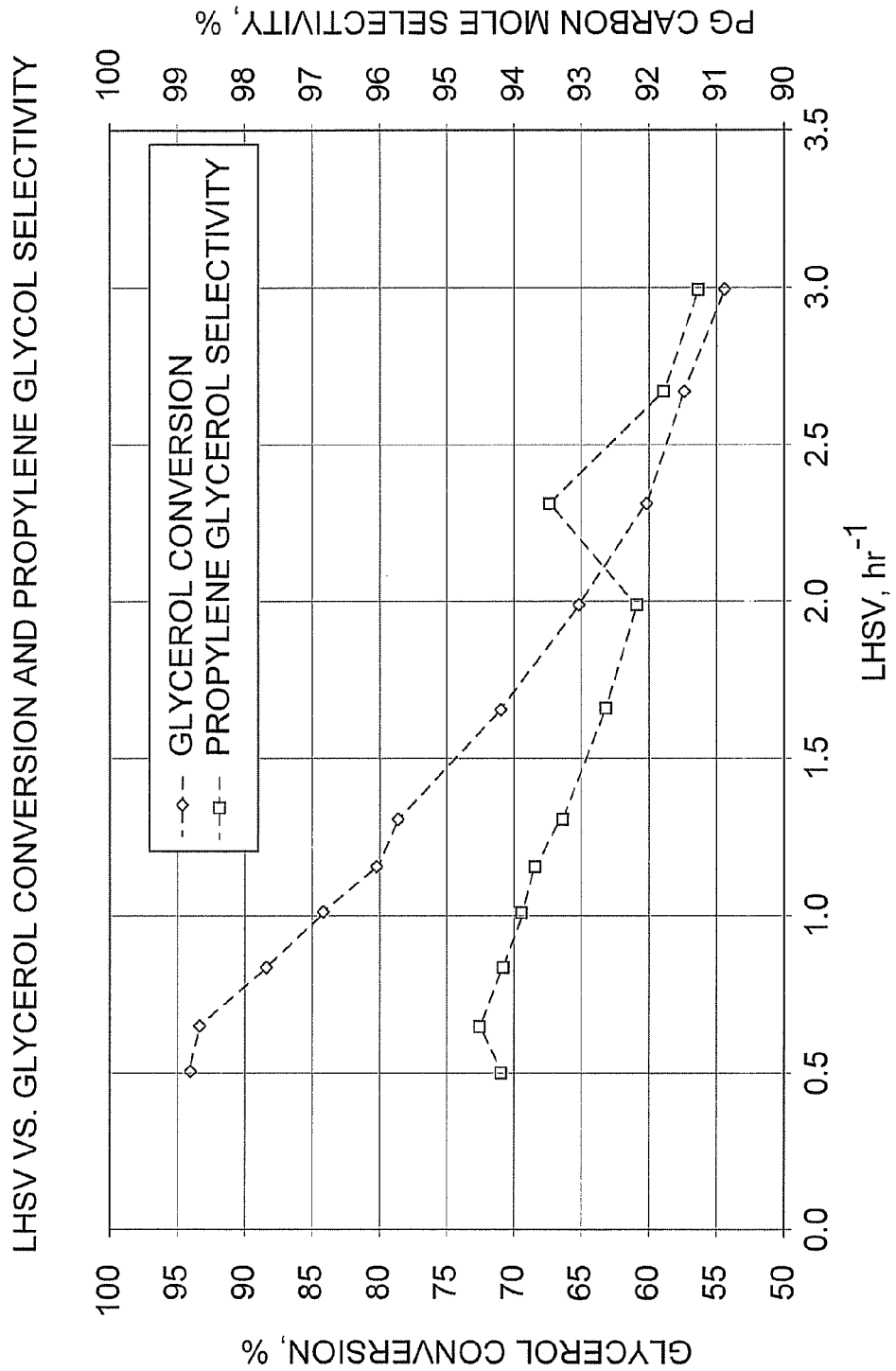
FIG. 10 is a plot of the impact varying reactor feed residence time on glycerol hydrogenolysis conversion and on propylene glycol selectivity.
Figure 11:
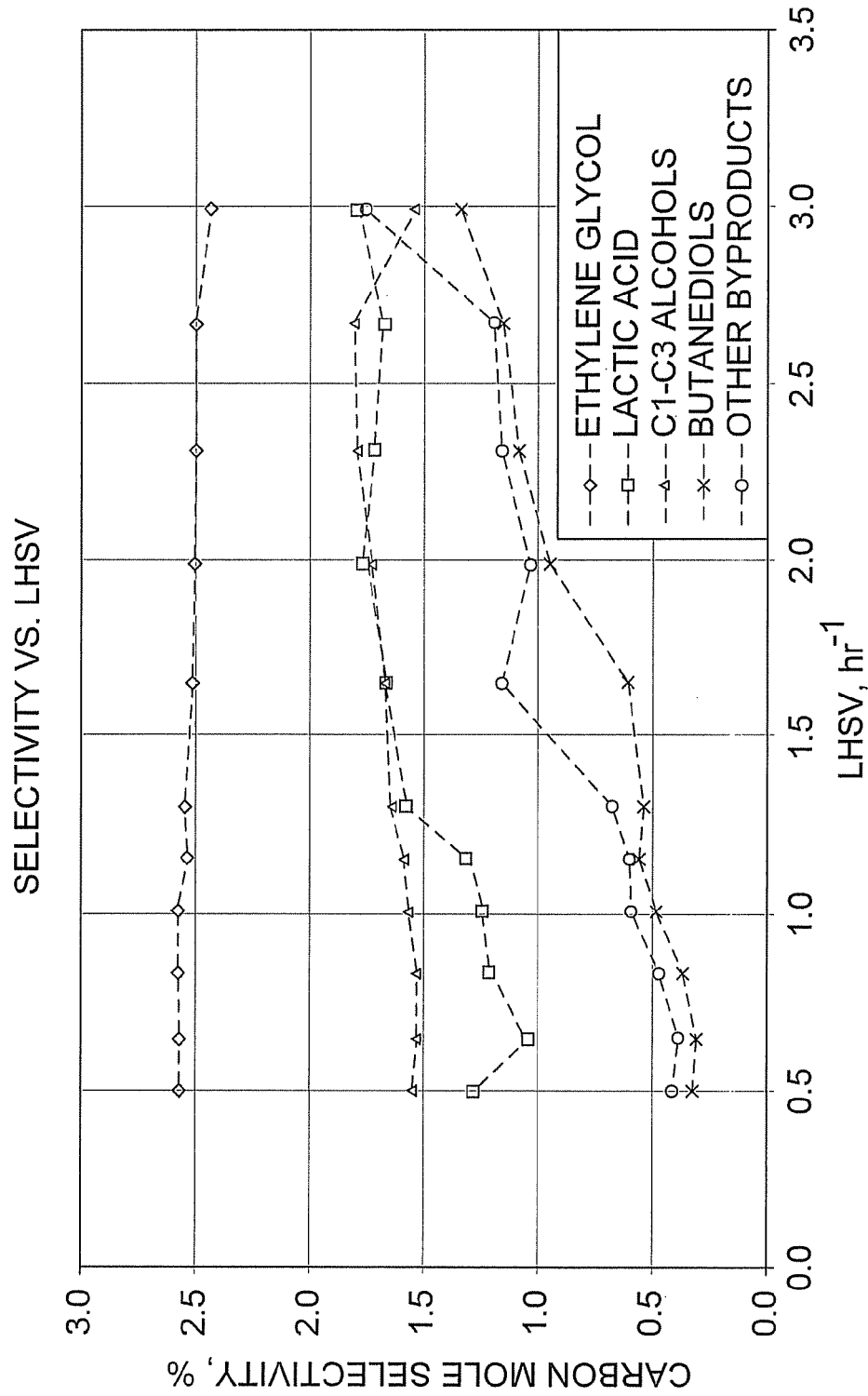
FIG. 11 is a plot of the impact of varying reactor feed residence time on glycerol hydrogenolysis byproduct selectivities.

The glycerol conversion and propylene glycol selectivity over the range of LHSVs is plotted in FIG. 10. Byproduct selectivities over the LHSV range are plotted in FIG. 11. Surprisingly, both the glycerol conversion and propylene glycol selectivity improved with decreasing LHSV at 356° F. The LHSV effect has been demonstrated with both USP glycerol and commercial glycerol feedstocks. More importantly, at longer residence times the butanediol selectivity is lower. Hence by operating at lower LHSV and temperatures both the glycerol conversion and propylene glycol selectivity can be maximized while minimizing the two critical byproducts (ethylene glycol and butanediol).

The invention claimed is:

1. A method for converting glycerol into propylene glycol, the method comprising the steps of:
    directing a glycerol feed to a feed blending section;
    combining a base with the glycerol feed in the feed blending section to form a basic glycerol containing feed stream having a pH of about 10 or greater;
    directing the basic glycerol containing feed stream and a hydrogen containing gas to a hydrogenolysis reaction section including at least one reactor and into contact with a glycerol conversion catalyst loaded in the at least one reactor, wherein the at least one reactor is operating at glycerol conversion conditions effective to form a reaction section product including propylene glycol, and wherein the glycerol conversion conditions include an average catalyst bed temperature of from about 325 to about 375° F. and a reactor pressure of from about 1500 to about 2000 psig;
    directing the reaction section product including propylene glycol to a separator to form a hydrogen rich separator off gas and a separator liquid product including propylene glycol; and
    directing the separator liquid product to a purification section and processing the separator liquid in the purification section by the further steps of:
        i. directing the separator liquid product to a unit operation to remove water and $C_1$-$C_3$ alcohols from the separator liquid product and to form an essentially water free product including propylene glycol and precipitated salts; and
        ii. directing the essentially water free product including propylene glycol and precipitated salts to a solid/liquid separator to form an essentially solids free product including propylene glycol.

2. The method of claim 1 wherein the separator liquid product is neutralized before water is removed by combining the separator liquid product with an amount of acid effective to form a neutralized separator liquid product having a pH of about neutral to about 7.5 and including propylene glycol.

3. The method of claim 1 wherein the separator liquid product is neutralized after step (i) and before step (ii) by combining the essentially water free product with an amount of acid effective to form a neutralized separator liquid product having a pH of about neutral to about 7.5 and including propylene glycol.

4. The method of claim 1 wherein the essentially solids free product including propylene glycol is further processed by fractionating the essentially solids free product in at least one fractionation column to recover a purified propylene glycol product.

5. The method of claim 4 wherein the essentially solids free product including propylene glycol further includes ethylene glycol, glycerol, and butanediols and is directed to a first fractionation column to form an overhead product including propylene glycol and butanediols and a bottoms product including ethylene glycol.

6. The method of claim 5 wherein the overhead product including propylene glycol and butanediols is not processed by a polishing step.

7. The method of claim 6 wherein the overhead product includes at least about 99.5 wt % propylene glycol.

8. The method of claim 4 wherein the essentially solids free product including propylene glycol further includes ethylene glycol, butanediols, and glycerol and is directed to a first fractionation column to form an overhead product including propylene glycol, butanediols, and ethylene glycol and a bottoms product including glycerol.

9. The method of claim 8 wherein the overhead product from the first fractionation column is directed to a second fractionation column to separate the ethylene glycol from the propylene glycol to form an essentially ethylene glycol free propylene glycol product.

10. The method of claim 1 wherein the glycerol conversion catalyst is selected from the group consisting of solid supported CoPdRe and solid supported NiRe.

11. The method of claim 1 wherein the glycerol conversion conditions include reactor glycerol liquid hourly space velocities of from about 0.1 to about 5.0 hr$^{-1}$ and a hydrogen to glycerol molar feed ratio of from about 2 to about 20.

12. The method of claim 1 wherein the glycerol feed includes fatty acids and is acidulated before being directed to the feed blending section.

13. The method of claim 12 wherein the glycerol feed including the fatty acids is a bio-based glycerol feed.

14. A method for converting glycerol into propylene glycol, the method comprising the steps of:

directing a combined feed including hydrogen and a basic glycerol feed that is adjusted to a pH of from about 10 to about 12 with an aqueous base to a hydrogenolysis reactor that includes at least one catalyst selected from the group consisting of a Ni/Re catalyst and a Co/Pd/Re catalyst, wherein the reactor is operating at glycerol conversion conditions effective to form a reaction section product including propylene glycol, and wherein a concentration of the aqueous base in the basic glycerol feed is increased over time and the glycerol conversion conditions include an average catalyst bed temperature that is maintained at about 375° F. or less while the concentration of the aqueous base in the basic glycerol feed is increased to maintain or increase glycerol conversion to propylene glycol; and directing the reaction section product including propylene glycol to a separator to form a hydrogen rich separator off gas and a separator liquid product including propylene glycol.

15. The method of claim 14 wherein the aqueous base comprises NaOH or KOH.

16. The method of claim 15 wherein the aqueous base comprises NaOH and the concentration of the aqueous phase in the basic glycerol feed is from about 0.5 wt % to about 5.0 wt %.

17. The method of claim 14 wherein the average catalyst bed temperature is from about 325° F. to about 375° F. and is not increased to maintain or increase the glycerol conversion.

18. A method for converting glycerol into propylene glycol, the method comprising the steps of:

directing a combined feed including hydrogen and a basic glycerol feed having a pH of from about 10 to about 12 to a hydrogenolysis reactor that includes a catalyst bed having at least one catalyst selected from the group consisting of a Ni/Re catalyst and a Co/Pd/Re catalyst, wherein the reactor operates at glycerol conversion conditions effective to form a reaction section product including propylene glycol with less than about 1.0 butanediol C mole % selectivity, wherein the basic glycerol feed includes at least 50 wt % of glycerol, and wherein the glycerol conversion conditions include an average catalyst bed temperature of about 375° F. or less and a reactor pressure of from about 1500 to about 2000 psig; and directing the reaction section product including propylene glycol to a separator to form a hydrogen rich separator off gas and a separator liquid product including propylene glycol.

19. The method of claim 18 wherein the glycerol conversion conditions include a reactor glycerol liquid hourly space velocity of from about 0.5 to about 2.0 hr$^{-1}$.

20. The method of claim 18 wherein the reactor pressure is about 1800 psig.

21. The method of claim 18 wherein the average catalyst bed temperature is from about 325° F. to about 375° F.

22. The method of claim 18 wherein the glycerol conversion conditions include the reactor pressure of from about 1600 psig to about 1900 psig, the average catalyst bed temperature of from about 325° F. to about 365° F., and a reactor glycerol liquid hourly space velocity of from about 0.5 to about 1.5 hr$^{-1}$.

* * * * *